United States Patent
Wang

(10) Patent No.: US 6,939,593 B2
(45) Date of Patent: Sep. 6, 2005

(54) MEDICAL DEVICES UTILIZING MELT-PROCESSIBLE POLY (TETRAFLUOROETHYLENE)

(75) Inventor: Lixiao Wang, Long Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/940,558

(22) Filed: Aug. 27, 2001

(65) Prior Publication Data
US 2003/0040702 A1 Feb. 27, 2003

(51) Int. Cl.[7] .......... B32B 1/08; B32B 27/08; F16L 11/04; A61M 25/01; A61M 25/10
(52) U.S. Cl. .......... 428/36.91; 428/36.9; 428/422; 604/96.01; 604/103.01; 604/403; 604/523
(58) Field of Search .......... 428/36.9, 36.91, 428/422; 604/96.01, 103.01, 403, 523

(56) References Cited

U.S. PATENT DOCUMENTS

| | | | |
|---|---|---|---|
| 4,859,836 A | * | 8/1989 | Lunk et al. .................. 219/548 |
| 5,141,800 A | * | 8/1992 | Effenberger et al. ........ 442/261 |
| 5,711,909 A | | 1/1998 | Gore et al. .................. 264/320 |
| 5,916,404 A | * | 6/1999 | Krause et al. ......... 156/244.23 |
| 5,944,937 A | * | 8/1999 | Fukumoto ................. 156/309.6 |
| 6,007,544 A | | 12/1999 | Kim .......................... 606/108 |
| 6,171,295 B1 | * | 1/2001 | Garabedian et al. ........ 604/524 |
| 6,451,005 B1 | * | 9/2002 | Saitou et al. ................ 604/526 |
| 6,478,814 B2 | | 11/2002 | Wang et al. ................ 123/1.12 |
| 6,508,805 B1 | * | 1/2003 | Garabedian et al. ........ 604/524 |
| 6,517,571 B1 | * | 2/2003 | Brauker et al. ............ 623/1.13 |
| 6,531,559 B1 | * | 3/2003 | Smith et al. ................ 526/255 |
| 2003/0023261 A1 | * | 1/2003 | Tomaschko et al. ........ 606/194 |

FOREIGN PATENT DOCUMENTS

WO  00/08071  8/1999

OTHER PUBLICATIONS

WO 01/58504 A1 (International Application No.: PCT/IL01/00131) (International Filing Date: Feb. 8, 2001) (Applicant: Sagitatarius AE LTD).

* cited by examiner

Primary Examiner—Harold Pyon
Assistant Examiner—Chris Bruenjes
(74) Attorney, Agent, or Firm—Vidas, Arrett & Steinkraus PA

(57) ABSTRACT

This invention relates to medical devices containing melt-processible polytetrafluoro-ethylene (PTFE) and methods of making same.

13 Claims, 2 Drawing Sheets

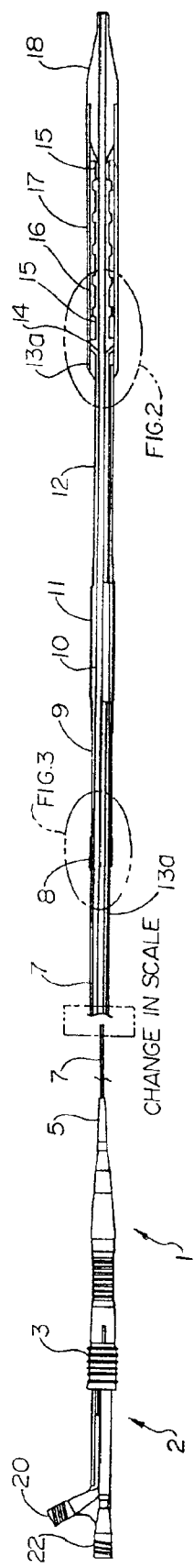
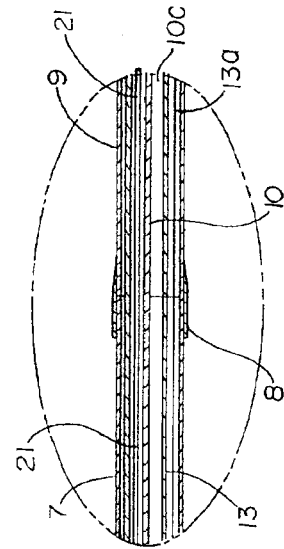
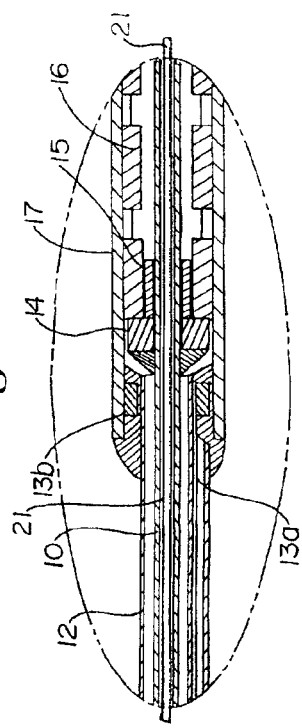

MEDICAL DEVICES UTILIZING MELT-PROCESSIBLE POLY (TETRAFLUOROETHYLENE)

FIELD OF THE INVENTION

This invention relates to medical devices made from melt-processible poly(tetrafluoroethylene) (MP-PTFE) and combinations of MP-PTFE and other fluoro polymers or other thermoplastics and methods for making the same.

BACKGROUND OF THE INVENTION

Certain medical devices have incorporated Poly (tetrafluoroethylene) (PTFE) in the past. However, this material was used as surface coatings and sheets having low friction characteristics. For example, coatings were used on guide wires and hypotubes for catheters. The material was not used to form parts of the medical device because it was not melt-processible. Some components of catheters incorporated PTFE, primarily as coatings, but the components were not primarily made from PTFE.

The making of medical devices using PTFE to be disclosed in the present application is achieved in part by using melt-processible PTFE, which is disclosed in PCT Publication WO 00/08071, published Feb. 17, 2000, and in an article in *Macromolecules*, Vol. 33, No. 17, 2000, pages 6460–6465. Both are incorporated herein by reference in their entirety. In these publications, the identification of a window of viscosities of PTFE is described that permits standard melt-processing of this unique polymer into mechanically coherent, tough objects. Therefore, PTFE had been characterized as "intractable" and "not melt-processible". Prior attempts at melt processing grades of PTFE were found to yield brittle products most of which could not be removed from a mold without fracture. As a result, PTFE could not be employed to melt-process articles of useful mechanical properties.

PTFE is well-known for, among other properties, its chemical resistance, high temperature stability, resistance against ultra-violet radiation, low friction coefficient and low dielectric constant. As a result, it has found numerous applications in harsh physico-chemical environments and other demanding conditions. Equally well-known are the intractability of this important polymer. Numerous textbooks, research articles, product brochures and patents state that PTFE was intractable because, above its crystalline melting temperature, it does not form a fluid phase that is of a viscosity that permits standard melt-processing techniques commonly used for most thermoplastic polymers (Modern Fluoropolymers, J. Scheirs, Ed. Wiley (New York), 1997; The Encyclopaedia of Advanced Materials, Vol. 2, D. Bloor et al. Eds., Pergamon (Oxford) 1994; WO 94/02547; WO 97/43102). Suitability of a polymer for standard melt-processing techniques may be evaluated, for example, through measurement of the melt-flow index of the material (cf. ASTM D 1238-88). Melt-processible polymers should, according to this widely employed method, exhibit at least a non-zero value of the melt-flow index, which is not the case for common PTFE under testing conditions that are representative of, and comparable to those encountered in standard polymer melt-processing. The extremely high viscosity of PTFE, reported to be in the range of $10^{10}$–$10^{13}$ Pa.s at 380° C., is believed to be associated, among other things, with an ultra-high molecular weight of the polymer, which has been estimated to be in the regime well above 1,000,000 g/mol and often is quoted to be of the order of 10,000,000 g/mol. In fact, it is claimed (Modem Fluoropolymers, J. Scheirs, Ed. Wiley (New York), 1997, p. 240) that "to achieve mechanical strength and toughness, the molecular weight of PTFE is required to be in the range $10^7$–$10^8$ g/mol . . . ". Due to this high viscosity, common PTFE was processed into useful shapes and objects with techniques that are dissimilar to standard melt processing methods. Rods, sheets, membranes, fibers and coatings of PTFE were produced by, for example, ram-extrusion, pre-forming and sintering of compressed powder, optionally followed by machining or skiving, paste-extrusion, high isostatic pressure processing, suspension spinning, and the like, and direct plasma polymerization. Unfortunately, these methods generally were less economical than common melt-processing, and, in addition, severely limited the types and characteristics of objects and products that can be manufactured with this unique polymer. For example, common thermoplastic polymers, such as polyethylene, isotactic polypropylene, nylons, poly(methylmethacrylate) polyesters, and the like, can readily be melt-processed into a variety forms and products that are of complex shapes, and/or exhibit, for example, some of the following characteristics: dense, void-free, thin, clear or translucent; i.e. properties that were not readily, if at all, associated with products fabricated from PTFE.

The above drawback of PTFE has been recognized virtually since its invention, and ever since, methods had been developed to circumvent the intractability of the polymer. However, a penalty is paid in terms of some or all of the outstanding properties of the homopolymer PTFE, such as reduced melting temperature and thermal and chemical stability.

Additional methods to process the PTFE homopolymer include, for example, the addition of lubricants, plasticizers, and processing aids, as well as oligomeric polyfluorinated substances and hydrocarbyl terminated TFE-oligomers (for example, Vydax® 1000) (U.S. Pat. Nos. 4,360,488; 4,385,026 and WO 94/02547). The latter method, however, is directed to the improvement of the creep resistance of common PTFE which results in a bimodal morphology with two distinct melting temperatures, and generally does not lead to homogeneous PTFE compositions that can be melt processed according to standard methods. For example, only a hot-compression molding method is prior to WO 00/08071 known for mixtures of standard PTFE and Vydax® 1000, that preferably is carried out in the narrow temperature range between about 330° C. to 338° C. The other aforementioned additions of lubricants, plasticizers, and processing aids also do not yield truly melt-processible PTFE compositions. Solution processing, at superautogeneous pressure, of PTFE from perfluoroalkanes containing 2–20 carbon atoms has been disclosed in WO 94/15998. The latter process is distinctly different from melt-processing methods. Also disclosed is dispersion, and subsequent melt-processing of standard PTFE into thermoplastic (host-) polymers such as polyetheretherketone and polyphenylene sulfide (WO 97/43102) and polyacetal (DE 41 12 248 A1). The latter method compromises important physico-chemical properties of the resulting composition, when compared to neat PTFE, or requires uneconomical and cumbersome removal of the host material.

There exist PTFE grades of low molecular weight and of low viscosity. These grades, which are often are referred to as micropowders, commonly are used as additives in inks, coatings and in thermoplastic and other polymers to impair, for example, nucleation, internal lubrication or other desirable properties that, in part, stem from the unique physico-chemical properties of the neat PTFE. Low molecular weight PTFE grades, in their solid form, unfortunately, exhibit extreme brittleness and, according to at least one of the suppliers, these PTFE grades "are not to be used as molding or extrusion powders" (Du Pont, Zonyl@ data sheets andurl:http://www.dupont.com/teflon/fluoroadditives/about.html—Jul. 7, 1998).

WO 00/08071 provided for the need to develop melt-processible, thermoplastic poly(tetrafluoroethylene)s to exploit the outstanding properties of this polymer in a wider spectrum of product forms, as well as to enable more economical processing of this unique material was provided for by the invention of WO 00/08071, as mentioned above. It was found that poly(tetrafluoroethylene)s of a particular set of physical characteristics provide a solution to the above, unsatisfactory situation. WO 00/08071 provided a melt-processible, thermoplastic PTFE compositions of good mechanical properties comprising PTFE grades that are characterized as having a non-zero melt-flow index in a particular range. As used hereinafter, the indication "good mechanical properties" means the polymer has properties suitable for use in thermoplastic applications, preferably including applications such as melt-processed thermoplastic formed into unoriented, solid fibers or films exhibiting an elongation at break of at least 10%, determined under standard ambient conditions at a rate of elongation of 100% per min. Further aspects regards MP-PTFE can be found in WO 00/08071.

The present invention utilizes the findings of WO 00/0871 in a novel and non-obvious manner, the details of which are disclosed below. All U.S. patents and applications all other published documents mentioned anywhere in this application are incorporated herein by reference in their entirety.

Without limiting the scope of the invention in any way, the invention is briefly summarized in some of its aspects below.

SUMMARY OF THE INVENTION

This invention relates to medical devices made from melt-processible poly(tetrafluoroethylene) (MP-PTFE) and combinations of MP-PTFE and other fluoro polymers or other thermoplastics and methods for making the same. Certain medical devices have incorporated Poly(tetrafluoroethylene) (PTFE) in the past. However, this material was used typically in sheets in cooperation with other materials and was used as a separate layer, as well as a coating. The present invention removes the need for the extra layer or coating of PTFE by making the medical parts themselves out of PTFE, and mixtures comprising PTFE. Among other embodiments, the present invention provides for extrusions over a guide wire and coextrusions to form multiple layer tubes for catheters.

The making of medical device parts using PTFE in the present application is achieved in part by using melt-processible PTFE, which is disclosed in PCT Publication WO 00/08071, published Feb. 17, 2000, and in an article in *Macromolecules*, Vol. 33, No. 17, 2000, pages 6460–6465. Both are incorporated herein by reference in their entirety.

The present invention contemplates extrusions and coextrusions of the MP-PTFE alone or in blends with other components to make the medical device parts. The resulting parts exhibit low friction, ease of movement of the parts and good trackability of the devices within the body.

BRIEF DESCRIPTION OF THE FIGURES

FIG. 1 shows a side view of a catheter according to the invention having a loaded stent including a cross section view of the distal portion thereof and a side view of the proximal end of a catheter according to the invention showing the manifold portion thereof.

FIG. 2 shows a partial cross section of the distal portion of the catheter of FIG. 1.

FIG. 3 shows a partial cross section of the catheter of FIG. 1.

DETAILED DESCRIPTION OF THE INVENTION

Figure 4:
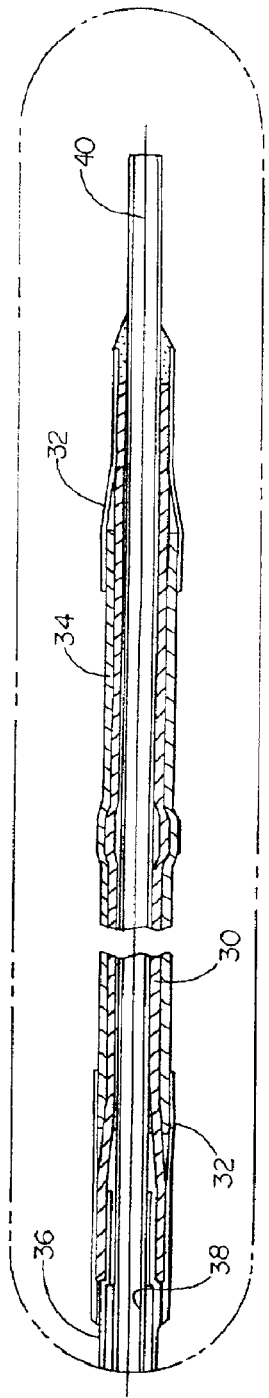
FIG. 4 shows a partial cross section of a balloon catheter for stent delivery.

While this invention may be embodied in many different forms, there are described in detail herein specific embodiments of the invention. The present disclosure is an exemplification of the principles of the invention and is not intended to limit the invention to the particular embodiments illustrated.

The present invention refers to medical devices which are well known. As such, figures are not included since they are not necessary for one skill in the art to understand the invention. However, examples of medical devices referred to herein can be found in many patents. Examples of catheters may be found in U.S. Pat. Nos. 5,980,533, 5,534,007 and 5,833,706. Stent delivery systems may also be found in U.S. Pat. No. 5,702,364. It should also be understood that the present invention also applies to plain old balloon angioplasty (POBA) catheters.

The inventive medical systems disclosed herein may also be provided with any of the features disclosed in U.S. Pat. No. 6,096,056, U.S. Pat. No. 6068,634, U.S. Pat. No. 6,036,697, U.S. Pat. No. 6,007,543, U.S. Pat. No. 5,968,069, U.S. Pat. No. 5,957,930, U.S. Pat. No. 5,944,726, U.S. Pat. No. 5,653,691 and U.S. Pat. No. 5,534,007. It should also be understood that the materials used may be any of those materials known in the art where applicable.

The stent delivery system may also comprise various coatings as are known in the art, including lubricious coatings to facilitate movement of the various parts of the system. More information concerning suitable coatings may be found in U.S. Pat. No. 5,443,907, and U.S. application Ser. Nos. 08/382,478, 09/306,939 and 09/316,502.

The products contemplated according to the present invention are numerous, and cover vastly different fields of applications. Components of catheters and other medical devices of interest include, but are not limited to, guide wires, guide catheters, diagnostic catheters, introducing sheaths for catheters, balloons, inner and outer shafts of catheters, stent retaining sleeves, stent protective sheaths, biopsy forceps, medical tubes, vena cava filters, implantable drug delivery devices and general implants, such as PTFE coated stents, pace maker leads. The present invention discloses the utilization of PTFE as the primary material in the construction of various medical devices without the difficulties or obstacles the material offered in the past. In particular, the PTFE may be used to form at least parts of the medical devices where low frictional surfaces are desired. The PTFE grades according to the present invention can be readily processed into mechanical coherent, tough, thin, dense and/or translucent objects useful in medical devices The PTFE's and their characteristics according to the present invention generally are polymers of tetrafluoroethylene. However, the present invention contemplates the scope of PTFE's as described in PCT Publication WO 00/08071.

The melt flow rate (MFR) of MP-PTFE is limited to 0.2–2.5 g/10 minutes. This makes the MP-PTFE not as strong as it should be. However, the low friction surface of the PTFE is highly advantageous in the medical industry. Benefits include, but are not limited to, good wire movement for such things as guide wires, improved trackability of medical devices and overall lower friction between part, such as in the case of inner and outer shafts for catheters. As such, the present invention contemplates mixtures or blends producing a bimode distribution. By way of example, the MP-PTFE can be made using blends of standard PTFE resin (10–80% wt having a MFI=10–1200 g/10 min or larger) and PTFE micropowder (2–80% wt having a MFI=0–2. g/min).

The invention also contemplates coextrusions of MP-PTFE with other fluoro copolymers such as Teflon™ PFA and MFA and FEP or any other thermoplastics to form multiple layer tubes or balloons. PFA is a copolymer of tetrafluoroethylene with a perfluoroalkyl vinyl ether. MFA is a modified fluoroalkoxy similar to PFA. It is a copolymerization of tetrafluoroethylene and perfluoromethylvinylether. FEP is a fluorinated ethylene-propylene resin. Other thermoplastics include, but are not limited to, polyesters, polyamides and polyurethanes. Coextrusion tubes can be used in catheters, guide catheters, and diagnostic catheters, for example, but not limited to, inner, outer, proximal or distal shafts. The number of layers of the coextrusion may be dictated by the needs of the user and is not limited specifically to one number. Suitably, the layer adjacent to another surface is comprised of the MP-PTFE. For instance, the inner layer of an outer catheter is made of the MP-PTFE to prevent undue friction with other items traveling therethrough and the outer layer of an inner tube, shaft or guide wire to similarly reduce friction with an items surrounding them.

Preferably, once-molten PTFE grades according to the present invention that are recrystallized by cooling under ambient pressure at a cooling rate of 10° C./min in unoriented form have a degree of crystallinity of between about 1% about 60%, preferably between about 5% and about 60%, more preferably at least about 45% and not more than 55% o based on a value of 102.1 J/g for 100% crystalline PTFE (Starkweather, H. W., Jr. et al., J. Polym. Sci., Polym. Phys. Ed., Vol. 20, 751 (1982)).

Preferably, the PTFE grades according to the present invention are characterized by an MFI (380/21.6) between about 0.25 to about 2 g/10 min and a degree of crystallinity of once-molten and recrystallized unoriented material of between about 5%, preferably above 45% and less then about 60%, preferably less than 55%. More preferably, the PTFE polymer is a polymer having a single peak melting point temperature which is above 325° C. and is preferably a homogenous blend of polymers and/or homopolymer.

The PTFE grades of the present invention can be synthesized according to standard chemical methods for the polymerization of tetrafluoroethylene as described in detail in the literature (for example, W. H. Tuminello et al., Macromolecules, Vol. 21, pp. 2606–2610 (1988)) and as practiced in the art. Additionally, PTFE grades according to the present invention can be prepared by controlled degradation of common, high molecular weight PTFE, for example by controlled thermal decomposition, electron beam, gamma- or other radiation, and the like (Modem Fluoropolymers, J. Scheirs, Ed. Wiley (New York), 1997 the entire disclosure of which is hereby incorporated by reference). Furthermore, and as demonstrated in the present invention, the PTFE grades according to the present invention can be manufactured by blending of, for example, high melt-flow index grades with appropriate amounts of grades of a lower, for instance below 0.5 g/10 min, or even zero melt-flow index to yield mixed materials with values of the melt-flow index, viscosity or crystallinity in the desired range. Due to the relatively simple nature of the MFI-testing method, viscosity measurement and crystallinity determination, using, for example, these analytical tools, those skilled in the art of polymer blending can readily adjust the relative portions of the different PTFE grades to obtain the melt-processible, thermoplastic PTFE compositions according to the present invention.

The compositions according to the present invention optionally may include other polymers, additives, agents, colorants, fillers (eq:, reinforcement and/or for cost-reduction), property-enhancement purposes and the like, reinforcing matter, such as glass-, aramid-, carbon fibers and the like, plasticizers, lubricants, processing aids, blowing or foaming agents, electrically conducting matter, other polymers, including poly(tetrafluoroethylene), fluorinated polymers and copolymers, polyolefin polymers' and copolymers, and rubbes and thermoplastic rubber blends, and the like. Depending on the particular application, one or more of the above optional additional ingredients and their respective amounts are selected according to standard practices known to those skilled in the art of standard polymer processing, compounding and applications.

Processing

The PTFE compositions according to the present invention can be processed into useful materials, neat or compounded, single- and mufti-component shapes and articles using common melt-processing methods used for thermoplastic polymers that are well known in the art. Typical examples of such methods are granulation, pelletizing, (melt-) compounding, melt-blending, injection molding, melt-blowing, melt-compression molding, melt-extrusion, melt-casting, melt-spinning, blow molding, melt-coating, melt-adhesion, welding, melt-rotation molding, dip-blowmolding, melt-impregnation, extrusion blow-molding, melt-roll coating, embossing, vacuum forming, melt-coextrusion, foaming, calendering, rolling, and the like.

Melt-processing of the PTFE compositions according to the present invention, in its most general form, comprises heating the composition to above the crystalline melting temperature of the PTFE's, which, of once-molten material, typically are in the range from about 320° C. to about 335° C. (preferably less than 400° C.), although somewhat lower, and higher temperatures may occur, to yield a viscous polymer fluid phase. Unlike standard (ultra-high molecular weight) PTFE above its crystalline melting temperature, the PTFE grades according to the present invention form homogenous melts that can be freed from voids and memory of the initial polymer particle morphology. The latter melt is shaped through common means into the desired form, and, subsequently or simultaneously, cooled to a temperature below the crystalline melting temperature of the PTFE's, yielding an object or article of good and useful mechanical properties. In one preferred embodiment, shaped PTFE melts are rapidly quenched at a cooling rate of more than 10° C./min, more preferably more than 50° C./min, to below the crystallization temperature to yield objects, such as fibers and films, of higher toughness.

Certain articles, such as, but not limited to, fibers and films made according to the present invention optionally may, subsequently, be drawn or otherwise, deformed in one or more directions, embossed, and the like to further improve the physico-chemical, mechanical, barrier, optical and/or surface properties, or be otherwise post-treated (for instance, quenched, heat treated, pressure treated, and/or chemically treated). The above methods and numerous modifications thereof and other forming and shaping, and post-processing techniques are well know and commonly practiced. Those skilled in the art of processing of thermoplastic polymers are capable of selecting the appropriate melt-processing and optional post-processing technology that is most economical and appropriate for the desired end product, or product intermediate.

The following descriptions are given as particular examples of parts of medical devices which may be made via the processes of the invention and to demonstrate the practice and advantages thereof. It is understood that the examples are given by way of illustration and are not intended to limit the specification or the claims that follow in any manner. A description of the figures will be given first to describe the basic parts of certain catheters.

FIG. 1 shows such a pull back stent delivery catheter, generally designated as 1. Generally, as a summary of U.S. Pat. Nos. 5,534,007 and 6,042,588, which are incorporated herein by reference, catheter 1 has a manifold 2 comprising a flush 20 and guide wire 22 access, a guide wire 21, a sheath actuator 3, which allows the user to retract the deployment sheath 17, and a strain relief portion 5. Extending distally, the manifold 2 is connected to the proximal shaft 7, which is the primary focus of the present invention, which is connected to the midshaft 9, preferably made of polyethylene. The midshaft is connected to the optional, but preferable, accordion shaft 11, which is in turn connected to the distal shaft 12. The distal portion, which is connected to the distal portion of the distal shaft, comprises the distal tip 18, the deployment sheath 17, the stent 16, marker bands 15 and a bumper 14. The combined shafts house a guide wire inner shaft 10, a guide wire 10a, a pull back wire lumen 13, a pull collar 13b, such as a hypotube, and a pull back wire 13a, which is connected to the deployment sheath 17 for release of the stent 16. A hypotube may be formed from an flat sheet, rolled into a cylinder and welded or the like. The length of the tube may vary based on the prescribed use.

Typically, a guide catheter covers the proximal shaft, which when inserted into the body follows a relatively linear path, but still must absorb the force built up from the more flexible distal portion carrying the more rigid stent portion through a more tortuous pathway. Greater detail of the distal portion is shown in FIG. 2. Further explanation of these sections may be found in U.S. Pat. No. 5,534,007.

FIG. 3 shows the connection between the proximal shaft 7 and the midshaft 9, or optionally the distal shaft 12. The sections are preferably adhered together via an overlapping shaft sleeve 8 using a urethane bond or welded. The Cobraid guide wire inner shaft 10 (polyimide shaft with stainless steel braid from HVT Technologies), the pull back wire lumen 13 and the pull back wire can also be more easily seen.

FIG. 4 shows the distal end of a balloon catheter having a balloon 30, a pair of retaining sleeves 32 and a loaded stent 34. Such devices are well known in the art.

Figure 5:
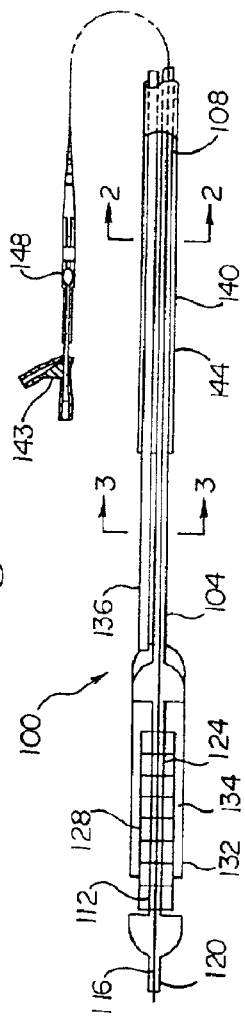
FIG. 5 shows a schematic side view of an embodiment of a stent delivery system having a loaded stent including a cross-sectional view of the distal portion thereof and a side view of the proximal end of a stent delivery system showing the manifold portion thereof.

FIG. 5 illustrates a system 100 which is disclosed in U.S. application Ser. No. 09/681,157, filed Feb. 1, 2001, and incorporated herein by reference in its entirety. The system includes an inner tube 104 with a proximal end 108 and a distal end 112. Distal end 112 terminates in tip 120 which may be attached thereto or may be a part of the inner tube itself. Inner tube 104 may optionally have a guide wire 116 extending therethrough.

A medical device receiving region 124 is located at distal end 112 of inner tube 104. As shown in FIG. 5, medical device receiving region is a stent receiving region. Stent 128 is shown disposed about stent receiving region 124.

Also disposed about stent receiving region 124 of inner tube 104 is stent sheath 132. Stent sheath 132 provides for a stent chamber 134 in which stent 128 resides. Stent sheath 132 has a hypotube 136 extending proximally therefrom to the proximal end of the stent delivery system. Hypotube 136 serves as a stent sheath retraction device. Hypotube 136 has an opening therein allowing for the delivery of a flush fluid to stent chamber 134. Hypotube 136 and stent sheath 132 may be formed of one piece construction or may be joined together adhesively or otherwise.

Stent delivery system 100 further comprises an outer sheath 140 which extends from the distal end of the stent delivery system. Outer sheath 140 is disposed about a portion of inner tube 104 and a portion of hypotube 136 and terminates proximal to stent sheath 132.

As shown in the embodiment of FIG. 5, distal end 144 of outer sheath 140 is separated from proximal end of stent sheath 132 by at least the length of the stent.

In use, the distal end of stent delivery system 100 is inserted in a circulatory vessel. Stent receiving region 124 with stent 128 received thereabout is advanced to a desired region in a vessel. Stent sheath 132 is then retracted in a proximal direction by sliding hypotube 136 proximally using slide 141 in manifold 143 so that the stent sheath no longer covers the stent, thereby allowing for the deployment of the stent. Desirably, stent sheath 132 is retracted until it abuts distal end 144 of outer sheath 140.

Figure 6:
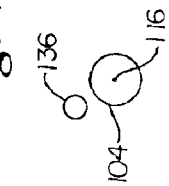
FIG. 6 shows a transverse cross-sectional view of the stent delivery system of FIG. 1 taken along line 2—2.
Figure 7:
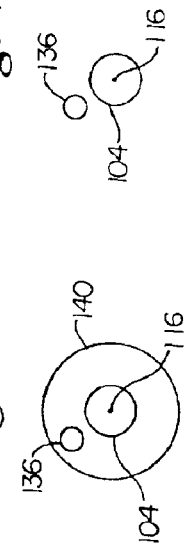
FIG. 7 shows a transverse cross-sectional view of the stent delivery system of FIG. 1 taken along line 3—3.

For the sake of clarity, FIG. 6 shows the stent delivery system in a transverse cross-section taken through outer sheath 140 along line 2—2 of FIG. 5 and FIG. 7 shows the stent delivery system in a transverse cross-section taken distal to outer sheath 140 along line 3—3 of FIG. 5.

Stent 128 may self-expand upon retraction of the sheath or may be expanded by the inflation of a balloon located underneath the stent (not shown in FIG. 5.). Thereafter, the stent delivery system is withdrawn with the stent deployed in the desired location in the bodily vessel.

Particular individual items of the above described catheters, in addition to the other mentioned items, through the processes described herein, are made to incorporate MP-PTFE. The MP-PTFE is extruded on the items or extruded to create the items. This may be done to provide a layer having a low COF rather than spraying PTFE, which is messy and expensive. The processes also removes the need for silicone coatings, such as on balloons.

FIGS. 1–3 illustrate examples of parts of catheters that may be extrusions coated with MP-PTFE. Outer shafts 7, 9, 12 and inner shafts (typically guide wire shafts) 10 are coated with PTFE by extruding MP-PTFE on the formed shafts. Both the inside and the outside of the shafts may be coated. As with other items, PTFE are suitably coated to surfaces which are adjacent to other moving surfaces to reduce friction. In this case, both the inner and outer surfaces of the shafts are coated. Inner and outer shafts may also be seen in FIGS. 4 (38, 36) and 5 (104,140).

Hypotubes are also coated using the present process. A hypotube may be formed from an flat sheet, rolled into a cylinder and welded or the like. The length of the tube may vary based on the prescribed use. Typically they are formed of metal. The MP-PTFE is extruded onto the hypotube prior to use. Two examples of hypotubes are shown in FIGS. 2 (13*b*) and 5 (136). The function of the hypotubes are described in the referenced patents above. The addition of the PTFE reduces the friction between the hypotubes and the objects which they move relative to.

Guide wires are also a target of the present invention. Examples may be seen in FIGS. 1–3 (21), 4 (40) and 5–7 (116). Guide wires are preferred to have a low COF due to the fact that the catheter has to slide along it. The present invention contemplates making low COF guide wires by extruding MP-PTFE onto the wire.

Another item which preferably exhibits a low COF is a sheath which covers a stent. A retractable sheath may be seen in FIGS. 1–3 (17). As described in the corresponding patent, the sheath slides off from over the stent 16. To reduce any snagging or friction problems, the sheath may co-extruded with MP-PTFE on both the inside and the outside.

Retaining sleeves 32, as seen in FIG. 4, may similarly be co-extruded with MP-PTFE. The layer of PTFE aids in smooth location of the catheter as well as a smooth release of the stent 34.

Catheter balloons, as seen in FIG. 4 at 30, can also be coextruded with MP-PTFE. A description of balloons can be found in U.S. Pat. No. 5,714,110 issued Feb. 3, 1998. The present process removes the use of coating balloons with a silicone oil. In the present process, a thin layer of PTFE is extruded over the surface of the balloon. One embodiment involves coextruding MP-PTFE with polyethylene terephthalate (PET) material to form the balloon.

Stents, as shown in the FIGS. as 16, 34 and 128, may also be coated with MP-PTFE where friction is a concern. The present invention also contemplates forming the stent from PTFE.

As mentioned above, well known implantable materials, such as grafts, the aforementioned stents and pace maker leads may be coated via extrusion with PTFE. Such a coating can replace silicone coatings. The coating of PTFE provides a low COF as well as increased insulation.

Many of the above items can be made of polyurethane. The present invention contemplates replacing polyurethane with PTFE and making the item by extruding MP-PTFE in the particular form. Examples include inner and outer shafts and guide catheters.

Having described specific embodiments of the present invention, it will be understood that many modifications thereof will readily appear or may be suggested to those skilled in the art, and it is intended therefore that this invention is limited only by the spirit and scope of the following claims.

All of the patent, applications or publications referred to above are herein incorporated by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependent claim format which creates a dependency from a prior antecedent-possessing claim other than the specific claim listed in such dependent claim below (e.g. claim 6 may be taken as alternatively dependent from any of claims 2–5, claim 4 may be taken as alternatively dependent from claim 3; etc.).

What is claimed is as follows:

1. A medical tube for inserting into the human body, comprising:

a tube comprising first, second, and third layers, in which the first layer is formed between the second and third layers, wherein the first layer is formed of a first material comprising a thermoplastic polymer comprising a co-polymer, wherein the copolymer is a fluoro copolymer chosen from the group consisting of a copolymer of tetrafluoroethylene with a perfluoroalkyl vinyl ether, a copolymerization of tetrafluoroethylene and perfluoromethylvinylether and a fluorinated ethylene-propylene resin, and a second layer is formed of a second material having a melt temperature, wherein the second material is a melt-processible poly (tetrafluoroethylene) composition, the melt-processible poly(tetrafluoroethylene) composition having a melt flow index value greater than 0 and less than 2.5 g/10minutes, and a third layer is formed of a third material having a melt temperature, wherein the third material is a melt-processible poly(tetrafluoroethylene) composition, the melt-processible poly (tetrafluoroethylene) composition having a melt flow index value greater than 0 and less than 2.5 g/10minutes, wherein the third layer is in direct contact with the first layer and wherein the first layer, the second layer, and the third layer are co-extruded at a temperature at or above the melt temperatures of the second and the third materials.

2. The medical tube of claim 1, wherein the medical tube is a catheter tube.

3. The medical tube of claim 2, the first layer having an inner and outer side, wherein the second layer is in contact with the inner side of the first layer.

4. The medical tube of claim 2, wherein the melt temperature of the second material exceeds 320° C.

5. The medical tube of claim 4, wherein the second material has an elongation to break of at least 10%.

6. The medical tube of claim 4, wherein the second material has a crystallinity of 1–55%.

7. The medical tube of claim 6, the third layer being tractable and having a peak melting temperature of at least 320 degrees C., an elongation to break of at least 10% and a crystallinity of 1–55%.

8. The medical tube of claim 1, wherein the three layers are thermally co-extruded above their melt temperatures.

9. The medical tube of claim 1, the first layer having an inner and outer side, wherein the second layer is in contact with the outer side of the first layer.

10. The medical tube of claim 1, wherein the tube is an inner catheter shaft.

11. The medical tube of claim 1, wherein the tube is an outer catheter shaft.

12. The medical tube of claim 1, wherein the tube is a catheter balloon.

13. The medical tube of claim 1, the second layer being tractable.

* * * * *